(12) United States Patent
Garland et al.

(10) Patent No.: US 6,256,406 B1
(45) Date of Patent: Jul. 3, 2001

(54) EXPOSURE COMPENSATION FOR DIGITAL RADIOGRAPHY SYSTEMS USING SELECTIVE SCANNING OF SENSOR ARRAYS

(75) Inventors: Harry T. Garland, Los Altos Hills; Gerald A. May, Saratoga, both of CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/154,534

(22) Filed: Sep. 16, 1998

(51) Int. Cl.[7] ................................................. G06K 9/00
(52) U.S. Cl. ............................................................ 382/132
(58) Field of Search ................................... 382/128, 131, 382/317, 318; 378/62, 96, 97, 95, 154, 49, 82, 5, 165, 145; 430/967, 966; 250/505.1

(56) References Cited

U.S. PATENT DOCUMENTS

| | | | | |
|---|---|---|---|---|
| 4,160,906 | * | 7/1979 | Daniels et al. ........................... | 378/97 |
| 4,454,606 | * | 6/1984 | Relihan ................................... | 378/97 |
| 4,542,519 | * | 9/1985 | Sugimoto ................................ | 378/19 |
| 4,953,192 | * | 8/1990 | Plewes .................................... | 378/146 |
| 5,054,048 | * | 10/1991 | Wang ...................................... | 378/146 |
| 5,067,144 | * | 11/1991 | Aitkenhead et al. .................. | 378/146 |
| 5,081,659 | * | 1/1992 | Dobbins, III .......................... | 378/98.2 |
| 5,444,756 | * | 8/1995 | Pai et al. ................................ | 378/98.8 |
| 6,031,892 | * | 2/2000 | Karellas ................................. | 378/98.3 |

* cited by examiner

Primary Examiner—Andrew W. Johns
Assistant Examiner—Shervin Nakhjavan
(74) Attorney, Agent, or Firm—Fenwick & West LLP

(57) ABSTRACT

Diagnostic x-ray images having uniform optical density are generated by selectively scanning (806) lines of pixels (402) in a sensor unit (202) used to capture x-ray images in a digital radiography system (200). By selectively scanning (806) the lines of pixels (402), the exposure time of such pixels can be controlled. The lines of pixels (402) are selectively scanned (806) according to exposure compensation profiles (600) for the anatomic regions of interest. The exposure compensation profiles (600) include an ordered sequence of exposure times which can be loaded into a programmable timer (306) coupled to read out circuitry (304) located in the sensor unit (202). The timer (306) uses this ordered sequence of exposure times to determine which pixel line to access next, and when to initiate that access. The exposure compensation profiles (600) can be generated (802) from empirical data by taking (800) preliminary low dose exposures of the body parts to be examined.

15 Claims, 8 Drawing Sheets

PANEL TIMING

| PIXEL LINE NUMBER | READOUT TIME (MILLISECS) |
|---|---|
| 1 | 10 |
| 2 | 15 |
| 3 | 28 |
| 4 | 32 |
| ... | ... |
| 1343 | 100 |
| 1344 | 110 |

602

| PIXEL LINE NUMBER | READOUT TIME (MILLISECS) |
|---|---|
| 1 | 10 |
| 2 | 15 |
| 3 | 28 |
| 4 | 32 |
| ... | ... |
| 1343 | 100 |
| 1344 | 110 |

604

| PIXEL LINE NUMBER | READOUT TIME (MILLISECS) |
|---|---|
| 1 | 120 |
| 2 | 125 |
| 3 | 135 |
| 4 | 142 |
| ... | ... |
| 1343 | 200 |
| 1344 | 210 |

606

| PIXEL LINE NUMBER | READOUT TIME (MILLISECS) |
|---|---|
| 1 | 120 |
| 2 | 125 |
| 3 | 135 |
| 4 | 142 |
| ... | ... |
| 1343 | 200 |
| 1344 | 210 |

EXPOSURE COMPENSATION FOR DIGITAL RADIOGRAPHY SYSTEMS USING SELECTIVE SCANNING OF SENSOR ARRAYS

RELATED APPLICATIONS

The subject matter of this application is related to U.S. patent application Ser. No. 09/153,937, entitled "Exposure Control For Digital Radiography Systems Using Charge Build-up in Sensor Array Pixels," filed on Sep. 16, 1998, by Harry Garland and Gerald May, which is incorporated by reference herein in its entirety.

The subject matter of this application is also related to U.S. patent application Ser. No. 09/154,179, entitled "Exposure Compensation For Digital Radiography Systems Using Spatial Look-up Tables," filed on Sep. 16, 1998, by Harry Garland and Gerald May.

TECHNICAL FIELD

This invention pertains to exposure compensation for digital radiography systems, and more particularly, to providing digital x-ray images having uniform optical density.

BACKGROUND ART

One of the most difficult tasks facing radiographers using conventional radiographic techniques (e.g., x-ray film) is producing a diagnostic image of uniform optical density when examining a body part that varies greatly in thickness or tissue composition. Conventional compensation techniques for density variation typically include a compensating filter. Compensating filters can be fabricated for many procedures, and therefore come in various sizes and shapes. They are usually constructed of aluminum or plastics.

One commonly used filter is a wedge filter. The wedge filter is used when exposing a body part, such as the human foot, to x-rays. For example, during examination of the foot, the wedge is positioned with its thick portion shadowing the toes and the thin portion toward the heel. The thick portion of the wedge absorbs excess radiation, thereby preventing overexposure of the toes. The thin portion of the wedge allows more radiation to penetrate the heel, thereby preventing underexposure of the heel. The overall benefit of using the wedge is to provide an image with uniform optical density.

Alternatively, wedge filters may be used to calibrate x-ray machines and evaluate radiography procedures. For example, when an object of varying thickness is x-rayed, a "step" wedge of the same material incorporating the same thickness variations can be used to determine sensitivity levels for each thickness. Step wedges comprise a continuous series of steps which can be manufactured to a customer's specifications for any height or width, step dimensions, total number of steps, and total height of wedge. By placing, for example, a penetrameter on each step of the wedge and exposing the step wedge to x-rays, the sensitivity levels for each thickness of an object can be determined.

Other types of compensating filters are commonly used with x-ray procedures and/or systems. These include "trough" filters for examining the chest, "bow-tie" filters for use with CT to compensate for the shape of the head or body, and "conic" filters (e.g., concave, convex) for use in digital fluoroscopy, where the image receptor and the image-intensifier tube are round.

Currently, digital radiography systems are beginning to replace conventional x-ray systems. Digital radiography systems provide high quality radiographs by capturing x-ray images with a sensor plate having a matrix or array of silicon detectors. The x-ray images can be transmitted to a diagnostic viewer or any other output device, or to any other location via, for example, an Ethernet interface.

The sensor plate provides several advantages over conventional x-ray film. For example, unlike conventional x-ray film, digital images can be previewed within a few seconds of x-ray exposure. Moreover, the sensor plate used in digital systems can capture most patient imaging areas with high resolution (e.g., 160×160 microns pixel size, with 4096 gray scale (12 bit) contrast). The sensor plate also covers a larger dynamic range than conventional x-ray film.

Like conventional x-ray film, digital radiography systems require exposure compensation for certain procedures. It is desirable therefore to have a system and method for compensating exposure deficiencies in a digital radiography system. Such a system and method should be easily integrated with existing digital radiography systems and provide simple, low cost exposure compensation without using conventional compensation filters.

SUMMARY OF THE INVENTION

The present invention pertains to exposure compensation for digital radiography systems using selective scanning of sensor arrays.

Diagnostic x-ray images having uniform optical density are generated by selectively scanning (806) lines of pixels (402) in a sensor unit (202) used to capture x-ray images in a digital radiography system (200). By selectively scanning (806) the lines of pixels (402), the exposure time of such pixels can be controlled. The lines of pixels (402) are selectively scanned (806) according to exposure compensation profiles (600) for the anatomic regions of interest. The exposure compensation profiles (600) include an ordered sequence of exposure times which can be loaded into a programmable timer (306) coupled to read out circuitry (304) located in the sensor unit (202). The timer (306) uses this ordered sequence of exposure times to determine which pixel line to access next, and when to initiate that access. The exposure compensation profiles (600) can be generated (802) from empirical data by taking (800) preliminary low dose exposures of the body parts to be examined

BRIEF DESCRIPTION OF THE DRAWINGS

These and other more detailed and specific objects and features of the present invention are more fully disclosed in the following specification, reference being had to the accompanying drawings, in which:

FIG. 6 is an illustration of an exposure compensation profile 600 for the sensor arrays 302a–d in FIG. 4 in accordance with the present invention;

DETAILED DESCRIPTION OF THE PREFERRED EMBODIMENTS

Figure 1:
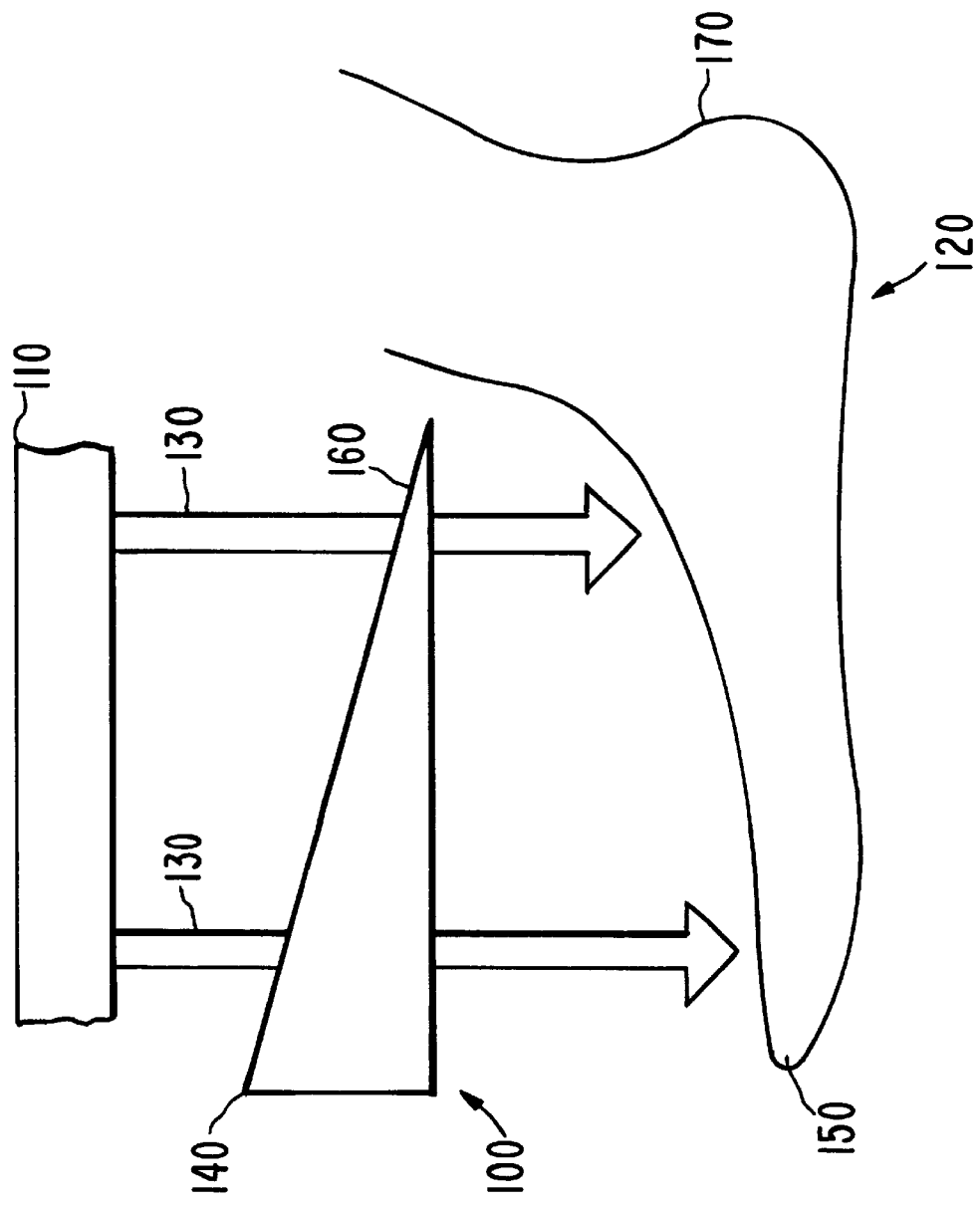
FIG. 1 is an illustration of a conventional wedge filter 100 for compensating the exposure of a human foot 120 to x-rays.

Referring to FIG. 1, there is shown an illustration of a conventional wedge filter 100 for compensating exposure of a human foot 120 to x-rays 130. The wedge filter 100 is positioned between an x-ray source 110 and the human foot 120. The wedge filter has a thick portion 140 and a thin portion 160. The thick portion 140 of the wedge filter 100 is positioned over the toes 150 of the foot 120, and the thin portion 160 of the wedge filter 100 is positioned toward the heel 170 of the foot 120. The wedge filter 100 typically is made of metal or plastic.

During examination, x-rays 130 generated by the x-ray source 110 are directed toward the human foot 120. The x-rays 130 penetrate through the foot 120 and impinge a sheet of x-ray film (not shown) disposed on the opposite side of the foot 120. The thick portion 140 of the wedge filter 100 absorbs a portion of x-rays 130 before they penetrate the toes 150, thereby preventing their overexposure. In contrast, the thin portion 160 of the wedge filter 100 allows more x-rays 130 to penetrate the heel 170, thereby preventing its underexposure.

A benefit of using the wedge filter 100 is to provide x-ray images with uniform optical density, thereby making such images suitable for diagnostic purposes. The wedge filter 100 is useful tool for certain procedures using conventional x-ray film systems. Pre-fabricated filters, such as the wedge filter 100, however, can be inconvenient and difficult to use accurately. For example, the placement of a fabricated filter with respect to a particular anatomic region can be time consuming, thereby extending the duration of the examination of the patient who may be critically ill or experiencing discomfort.

While the wedge filter 100 and the human foot 120 are examples referred to throughout the specification in relation to x-ray exposure compensation, the present invention is applicable to other types of compensation as well. These include, for example, "trough" filters for examining the chest, "bow-tie" filters for use with CT to compensate for the shape of the head or body, and "conic" filters (e.g., concave, convex) for use in digital fluoroscopy, where the image receptor and the image-intensifier tube are round.

Figure 2:
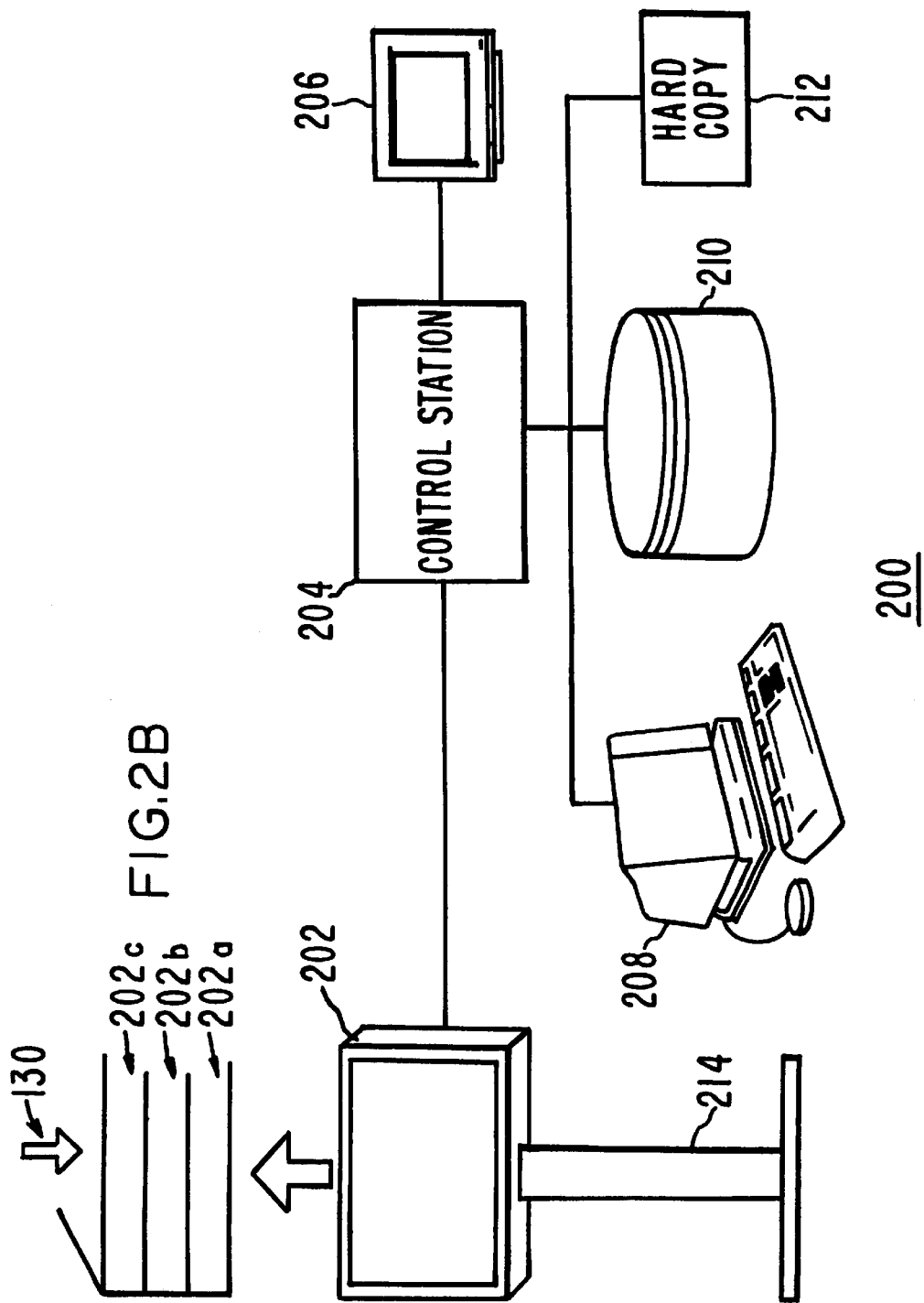
FIG. 2A is an illustration of one embodiment of a digital radiography system 200 in accordance with the present invention.
FIG. 2B is a sectional side view of the sensor unit 202 in FIG. 2A in accordance with the present invention.

Referring to FIG. 2A, there is shown a functional diagram illustrating one embodiment of a digital radiography system 200 in accordance with the present invention. The system 200 includes a sensor unit 202, a control station 204, an operation panel 206, a viewing workstation 208, an image archiver 210, and a hard copy output device 212. The sensor unit 202 is mounted on an upright stand 214 and coupled to the control station 204. A sectional side view of the sensor unit 202 in FIG. 2B shows three elements: a sensor plate 202a, a scintillator 202b, and a protective covering 202c. The sensor plate 202a includes a sensor array of pixels for capturing x-ray images. The term pixel (i.e., picture element), as used hereinafter, is the smallest part of an image that a computer printer or display can control. An image on a computer display can consist of hundreds of thousands of pixels, arranged in such a manner that they appear to be connected. For continuous-tone images, each pixel is assigned a numerical value (hereinafter also referred to as a "pixel value") that is directly mapped into a gray-scale palette and loaded in, for example, a video display adapter (VGA). The image can then be displayed in evenly spaced shades of gray.

The scintillator 202b is disposed on top of the sensor plate 202a to convert ionizing radiation from x-rays 130 into a visible light spectrum that the sensor plate 202a can detect. The protective covering 202c is disposed on the top of the scintillator 202b for protecting the sensor plate 202a from the environment.

The control station 204 is coupled to the sensor unit 202, the operation panel 206, the viewing workstation 208, the image archiver 210, and the hard copy output device 212. The control station 204 is for image processing and temporary storage of x-ray images.

The operation panel 206 is coupled to the control station 204 for primary image checking, data input of patient and exposure information, and selection of image processing.

The viewing workstation 208 is coupled to the control station 204, the image archiver 210, and the hard copy output device 212. The viewing workstation 208 is for assisting a radiologist in making a diagnosis based on x-ray images. The radiologist can view and compare new images with images stored in the image archiver 210.

The image archiver 210 is coupled to the control station 204, the viewing workstation 208, and the hard copy output device 212. The image archiver 210 provides long term storage of x-ray images.

The hard copy output device 212 is coupled to the control station 204, the image archiver 210, and the viewing workstation 208. The hard copy output device 212 provides hard copies of x-ray images.

During a patient examination, a patient's body part is placed between the sensor unit 202 and an x-ray source (not shown). Using the operation panel 206, a radiographer inputs patient and exposure information, selects a desired image processing technique, and previews the x-ray image. The body part is then exposed to x-rays from the x-ray source. The x-rays penetrate the body part and ultimately impinge the pixels disposed on the sensor plate. The pixels transform the x-ray energy into photocurrent which can be summed, for example, by an integrating amplifier, over a predetermined exposure time. This photocurrent typically is proportional to the effective x-ray intensity on the pixel. Most human body parts are composed of organic matter such as fluid, bone, cartilage, and soft tissue, and each type of matter absorbs x-rays at a different rate. Therefore, over a predetermined exposure time the intensity of x-rays across the sensor array will vary due to these absorption rates. This intensity can be quantified and assigned a numerical value indicative of a gray-scale which can be used by a computer to construct a continuous-tone x-ray image suitable for diagnostic purposes.

After the x-ray image is captured by the sensor unit 202, it can be transferred to one or more devices such as the viewing workstation 208, the image archiver 210, and the hard copy output device 212. These devices can assist the radiologist in her diagnosis of the patient.

The digital radiography system 200 described above provides several advantages over conventional film systems.

For example, it is much quicker to get an image using a digital radiography system. An image can be acquired in about six seconds. The image can be quickly previewed to determine if the correct exposure time was used. With conventional film systems, it takes several minutes for the film to develop. During this time, the doctor cannot release the patient until she is certain the x-ray was properly taken, thereby subjecting the patient to inconvenience and discomfort for an extended period of time.

Also, with a digital system a radiographer can apply image processing techniques after the image has been captured. The digital images can be stored in long-term archive and recalled at will for a comparative diagnosis. This is not true for film-based systems, where exposed film is stored off-site, thereby making it difficult to retrieve for comparative diagnosis.

Another advantage associated with digital systems is its large dynamic range. While film-based systems probably provide better spatial resolution than digital systems, in most cases the greater dynamic range of the sensor plates will typically outweigh any loss in spatial resolution.

Figure 3:
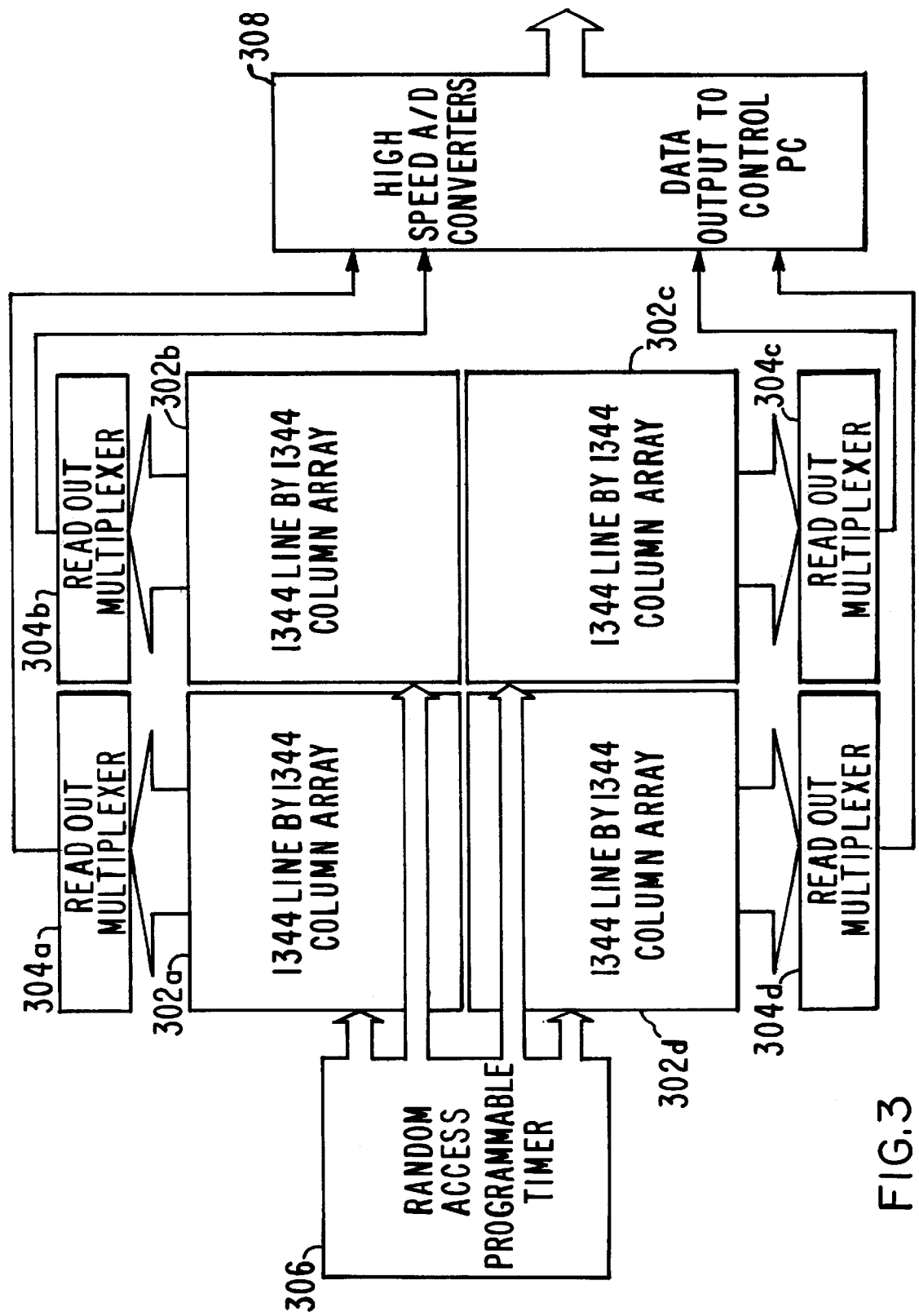
FIG. 3 is a functional block diagram illustrating one embodiment of the sensor unit 202 in FIG. 2 in accordance with the present invention.

Referring to FIG. 3, there is shown a functional block diagram illustrating one embodiment of a sensor unit 202 in accordance with the present invention. The sensor unit 202 is part of the digital radiography system 200 in FIG. 2, and is used for capturing x-ray images. In the preferred embodiment, the sensor unit 202 includes sensor plate 202a, read out multiplexers 304a–d, programmable timing generator 306, and analog-to-digital (A/D) converter 308. The sensor plate 202a further includes sensor arrays 302a–d. Each sensor array can be, for example, an 8½ square inch rectangular matrix of amorphous silicon photo sites (hereinafter also referred to as "pixels"). The pixels can be arranged in 1,344 lines and 1,344 columns. The sensor arrays 302a–d can be tiled together to form a larger 17 square inch matrix having 2,688 lines and 2,688 columns. This larger sensor array can provide a wide imaging size (e.g., 2,688×2,688 pixels; over 7 million microns) and high resolution (e.g., 160×160 microns pixel size, with 12 bit (4096 gray scale) contrast).

The sensor arrays 302a–d are coupled to read out multiplexers 304a–d, respectively. In this configuration, any individual pixel line in sensor arrays 302a–d is accessed randomly through its respective read out multiplexers 304a–d. These pixel lines can be read out while the patient is being exposed to x-rays. In other words, the x-ray image can be read out while the photocurrents from the pixels are being summed, thus enabling images to be read out from the sensor arrays 302a–d without blurring. This process is described in further detail below in conjunction with FIGS. 4A and 4B.

The read out multiplexers 304a–d are coupled to A/D converter 308 for converting the intensity values at each pixel to a digital representation. Each of the read out multiplexers 304a–d can be coupled to its own A/D converter 308, or alternatively, each read out multiplexer 304a–d can be further multiplexed to share one or more A/D converters. Each sensor array 302a–d can be coupled to a plurality of multiplexers to provide additional flexibility in reading individual pixel lines in the sensor arrays 302a–d.

The sensor arrays 302a–d are also coupled to random access programmable timer 306. The programmable timer 306 sends control signals to the sensor arrays 302a–d. The programmable timer 306 implements an exposure compensation profile for the particular body part being examined. The exposure compensation profile preferably includes an ordered sequence of exposure times for different portions of sensor arrays 302a–d. These exposure times are used to selectively scan pixels from the sensor arrays 302a–d, as described with respect to FIG. 6.

It is noted that the present invention is not limited to the configuration in FIG. 3, and other configurations are possible for reading pixel values and converting them to digital representations. For example, any number of sensor arrays, multiplexers, and A/D converters, or any equivalents of these devices, may be combined to implement the present invention.

Figure 4A:
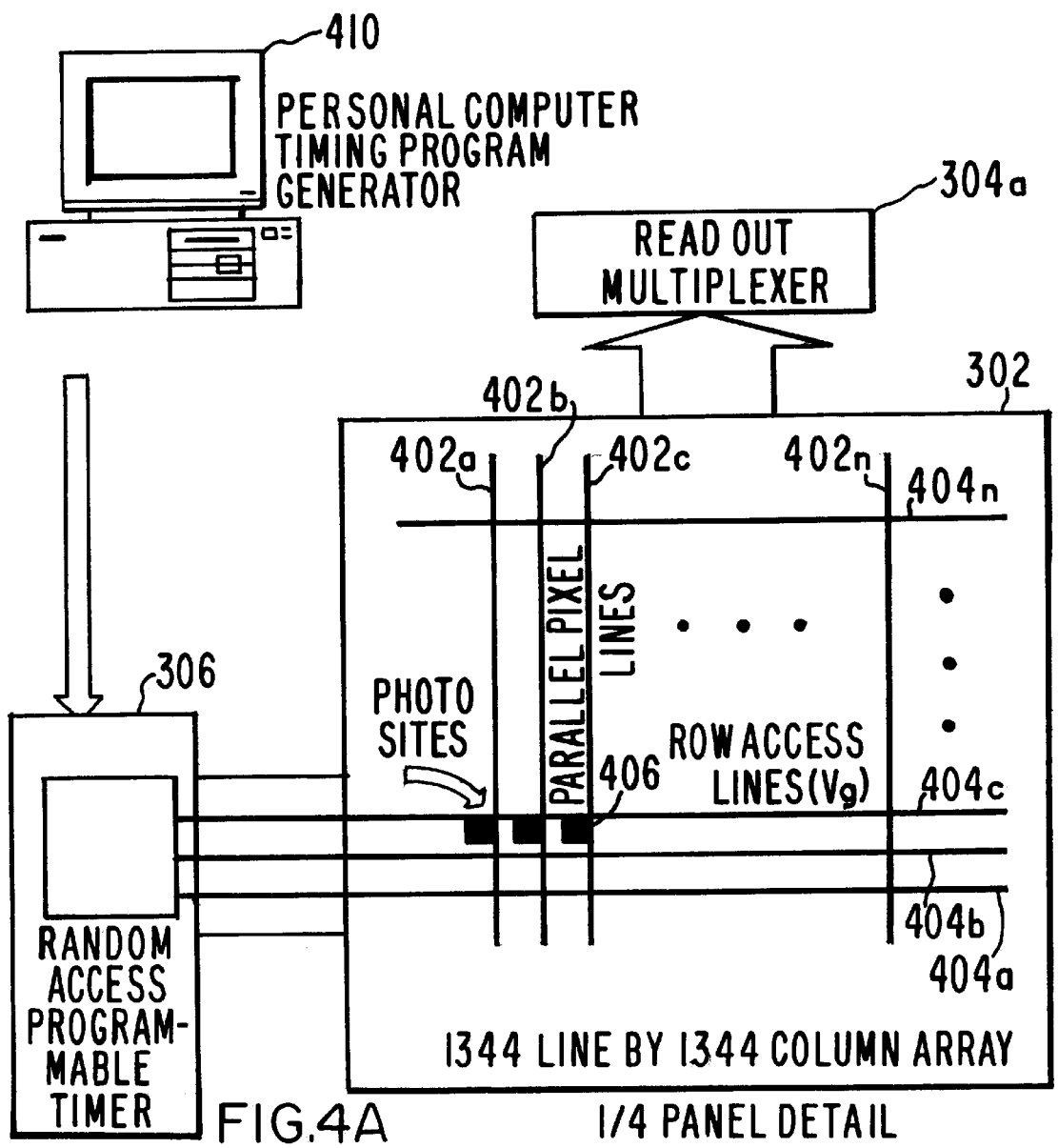
FIG. 4A is a functional block diagram illustrating one embodiment of the sensor array 302a in FIG. 3 in accordance with the present invention.

Referring to FIG. 4A, there is shown a functional block diagram illustrating one embodiment of the sensor array 302a in FIG. 3 in accordance with the present invention. The sensor array 302a is coupled to read out multiplexer 304a and the programmable timer 306. A plurality of pixels are disposed in the sensor array 302a in parallel pixel lines 402a–n, where n is the total number of pixel lines in the sensor array 302a. For example, pixel 406 is located on parallel pixel line 402c of the sensor array 302a. The parallel pixel lines 402a–n are coupled to row access lines 404a–n, where n is the total number of row access lines in the sensor array 302a. The row access lines 404a–n are coupled to the programmable timer 306. The programmable timer 306 is coupled to a timing program generator 410, which, for example, can be a personal computer (PC).

The timing program generator 410 generates an ordered sequence of exposure times for selectively scanning the parallel pixel lines 402a–n, via the row access lines 404a–n, while the patient's body part is being exposed to x-rays. The programmable timer 306 scans parallel pixel lines 402a–n from the sensor array 302a according to the ordered sequence of exposure times generated by the timing program generator 410. In other words, the exposure time of each pixel can be controlled by the order in which each pixel is scanned and read out of the sensor array 302a.

Referring again to FIG. 1, the pixels in the sensor array used to capture an image of toes 150 of foot 120 are read out of the sensor array before the pixels used to capture an image of heel 170 of foot 120 are read out. Thus, the toes 150 pixels, which are typically overexposed, have less time to integrate photocurrent than the heel 170 pixels, which are typically underexposed. Therefore, by selectively scanning and reading out pixel lines from the sensor array, an x-ray image having uniform optical density can be captured. This process is described in further detail in conjunction with FIG. 6.

Figure 4B:
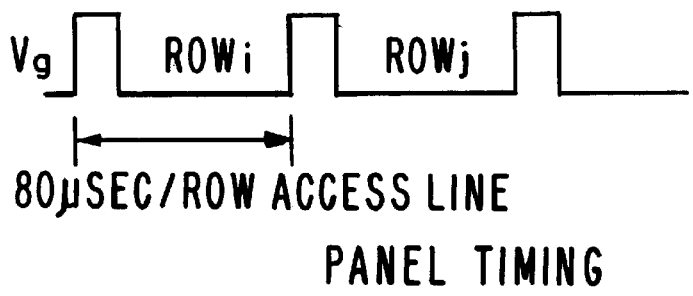
FIG. 4B is a timing diagram for scanning pixel lines in the sensor array 302a in FIG. 4 in accordance with the present invention.

Referring to FIG. 4B, there is shown a timing diagram for reading out pixels in accordance with one embodiment of the present invention. The timing diagram illustrates that each row access line 404a–n in the sensor array 302a takes a finite amount of time to read out (e.g., 80 μsec/row access line). This finite amount of time is substantially less than the total exposure time of the body part, which typically is hundreds of milliseconds. Because of these fast row access times, the rows of pixels can be selectively scanned and read out from the sensor array within the normal patient exposure time, which typically is short in duration to reduce the patient's exposure to x-rays.

Figure 5:
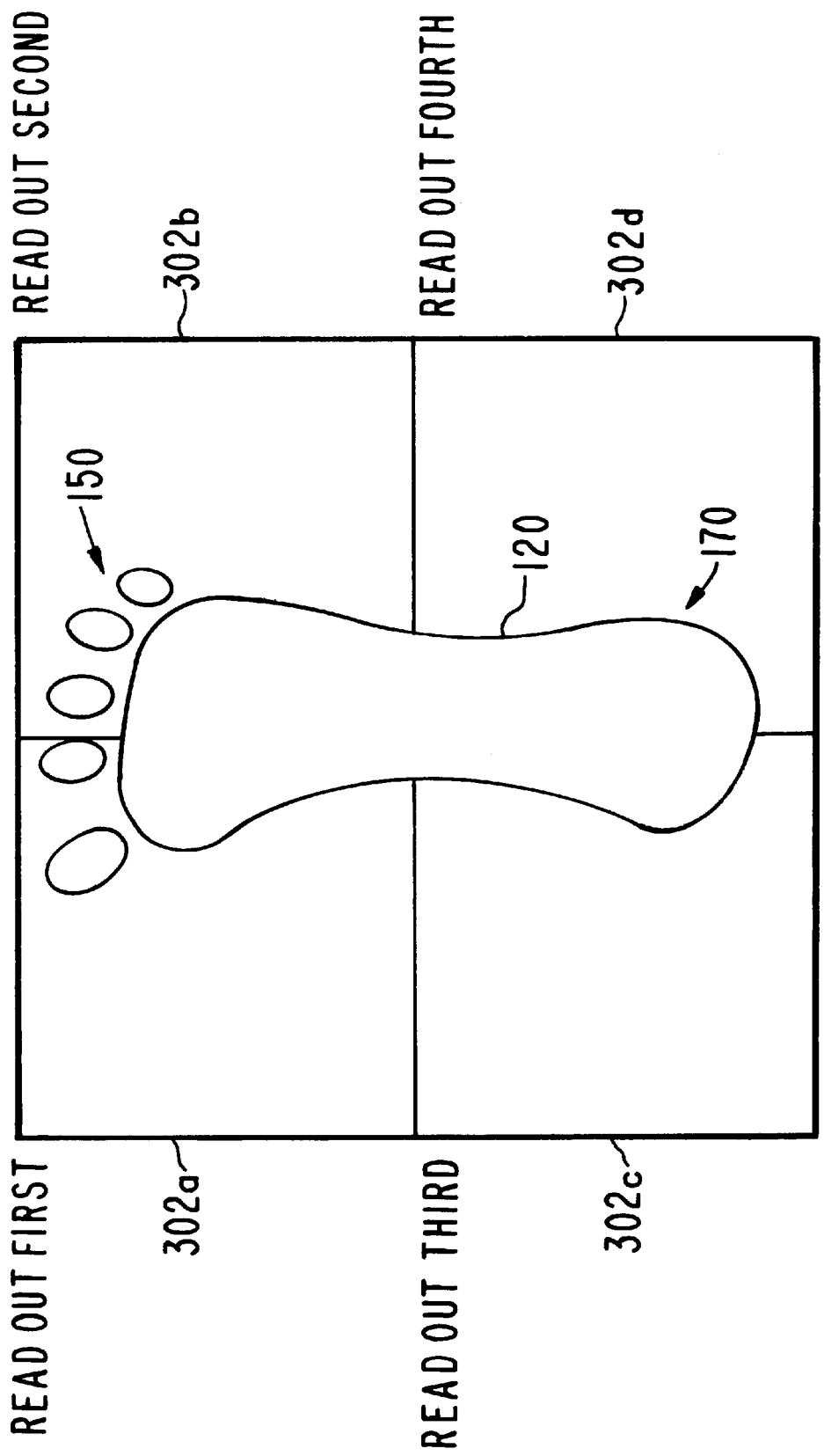
FIG. 5 is an illustration of selective scanning of the human foot 120 in FIG. 1 in accordance with the present invention.

Referring to FIG. 5, there is shown an illustration of one embodiment of a selective pixel scan from sensor arrays 302a–d in FIG. 3 in accordance with the present invention. A human foot 120 includes toes 150 and a heel 170. The heel 170 is thicker than the toes 150. To obtain an x-ray image of the foot 120 having uniform optical density, the pixel outputs in the sensor arrays 302a–d are read out in a predetermined sequence. That is, the pixels in sensor array 302a and 302b are read out first, followed by the pixels in sensor array 302c and 302d. In this particular sequence, the image is scanned line-by-line from top to bottom. As stated previously, the pixels can be scanned while their photocurrents are being integrated. Therefore, by selectively scanning the sensor arrays 302a–d, the exposure time of the heel 170 relative to the exposure time of the toes 150 can be adjusted to obtain an image having uniform optical density. Preferably, the scanning order is determined by exposure compensation profiles. These profiles can be derived for any body part and view angle using empirical generated data, as described below with respect to FIG. 7.

Referring to FIG. 6, there is shown an illustration of one embodiment of an exposure compensation profile 600 having exposure times for the sensor arrays 302a–d in FIG. 4 in accordance with the present invention. The exposure compensation profile 600 includes exposure time sequences 602 through 608 corresponding to the sensor arrays 302a–d, respectively. The exposure time sequences 602 and 604 each include a set of pixel line numbers {1 2 3 4 . . . 1343 1344}, each of which have a set of corresponding read out times {10 15 28 32 . . . 100 110}. The read out times are in milliseconds (ms). It takes about 110 ms to read out the pixel lines 1–1344 in sensor arrays 302a and 302b, which preferably are read out at the same time. Similarly, it takes about 110 ms to read out the pixel lines 1–1344 in sensor arrays 302c and 302d, which are also read out at the same time. Thus, in this preferred embodiment, it takes a total time of 210 ms to read out the entire sensor plate 202. During an examination of, for example, the human foot 120, each exposure time sequence 602 through 608 in the exposure compensation profile 600 is loaded into the programmable timer 306 to selectively scan pixel lines in the sensor arrays 302a–d.

Figure 7:
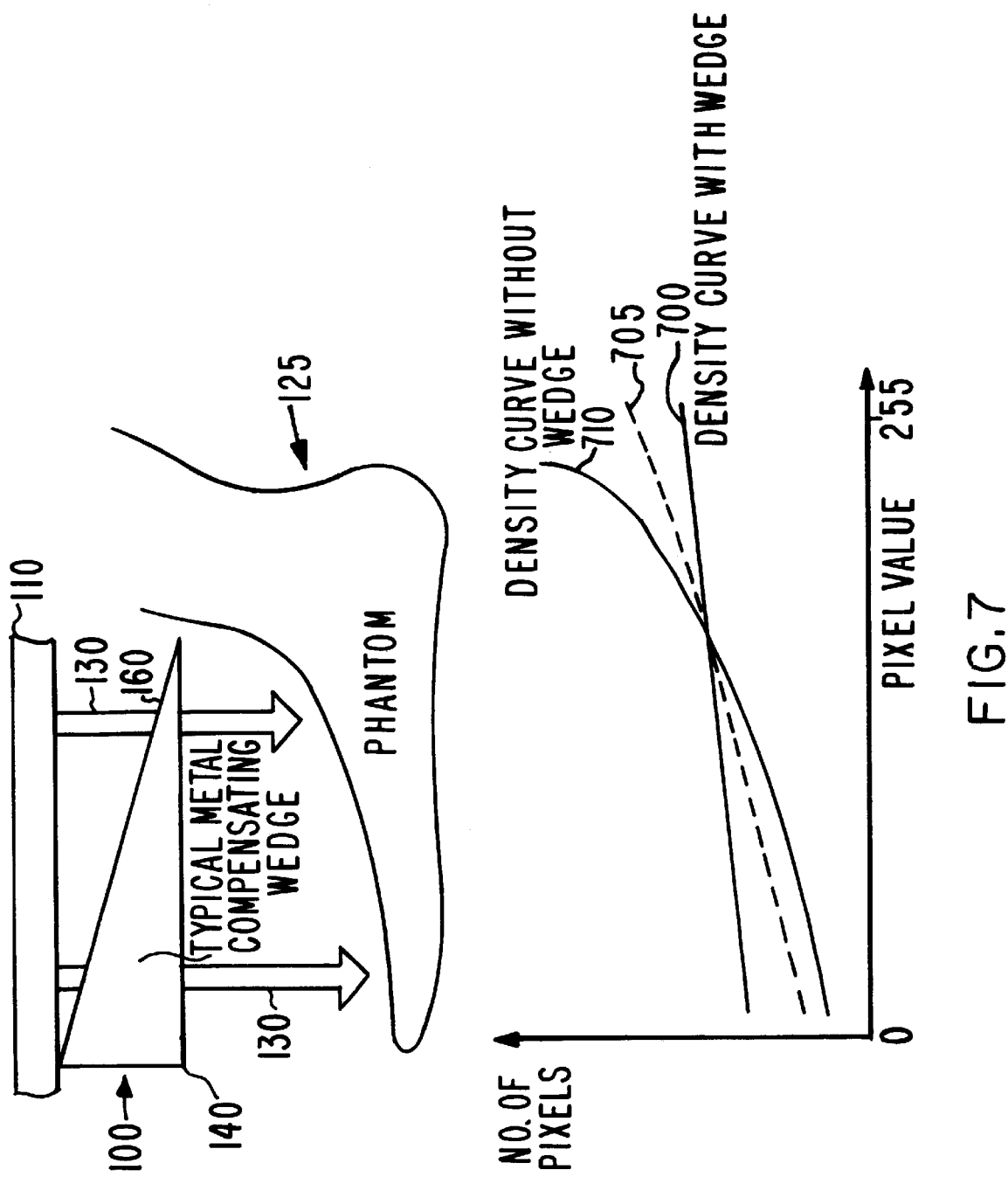
FIG. 7 is an illustration of the generation of exposure compensation profiles for the human foot 120 using empirical techniques in accordance with the present invention.

Referring to FIG. 7, there is shown an illustration of one embodiment of empirical generation of an exposure compensation profile for a human foot in accordance with the present invention. In this example, we assume the x-ray image is an eight-bit continuous tone image of the human foot 120, represented by 256 different levels of gray. These gray levels are indicated on the horizontal axis of the graph in FIG. 7. The vertical axis of this graph represents the number of pixels in the image having a particular gray level. The curves 700, 705, and 710 on the graph are the envelopes of image histograms, as described in Craig A. Lindley, *Practical Image Processing In C* (1991; John Wiley & Sons, Inc., NY), incorporated by reference herein in its entirety. A histogram is a graph of the distribution of pixel-intensity values (e.g., gray levels) for an image or a portion of an image.

To empirically generate an exposure compensation profile 600 for the human foot 120, a radiographer can generate a phantom image 125 of a human foot 120 with a conventional wedge filter 100 positioned between the x-ray source 110 and the human foot 120. The phantom image 125 can be generated using, in part, the techniques described in U.S. patent application Ser. No. 09/153,937 entitled "Exposure Control For Digital Radiography Systems Using Charge Build-up in Sensor Array Pixels," filed on Sep. 16, 1998, by Harry Garland and Gerald May, which is incorporated by reference herein in its entirety. For example, a preliminary low dose exposure of a real human foot 120 can be used to generate the phantom image 125. The preliminary exposure dose can be selected to have a negligible effect on the patient when compared to the normal dose used to generate a diagnostic image. The preliminary exposures can employ the lower part of the dynamic range of the sensor arrays 302a–d to create the phantom image 125. The phantom image 125 can be used to map out the area of anatomical interest (e.g., heel, toes) to create a virtual sensor array precisely positioned in the area of interest. Multiple preliminary phantom images can be averaged to reduce sensor noise which is greatest for low exposure times.

As illustrated by the graph shown in FIG. 7, the phantom image 125 has an optical density curve 700 that is linear due to the compensating effect of the wedge filter 100. The linear characteristic is indicative of an image having uniform optical density.

After the phantom image 125 is generated, a test series of read out sequences is executed on the phantom image 125, without the wedge filter 100 in the x-ray path. A first read out sequence typically will generate a non-linear optical density curve 710, as shown in FIG. 7. The series of read out sequences will continue until an optical density curve is generated that matches the linear optical density curve 700 generated with the wedge filter 100. A match between the curve 700 and a current optical density curve 705 is determined by comparing curve parameters (e.g., slope, intercept, polynomial coefficients). In other words, the test series determines the read out sequences that produces an optical density curve most nearly identical to the optical density curve 700. In the preferred embodiment, each readout sequence includes pixel line numbers and corresponding read out times, as described with respect to FIG. 6. Moreover, each read out sequence corresponds to one of the sensor arrays 302a–d.

This empirical method can be used to generate exposure compensation profiles for a number of different types of x-ray procedures that use, for example, "trough" filters for examining the chest, "bow-tie" filters for use with CT to compensate for the shape of the head or body, and "conic" filters (e.g., concave, convex) for use in digital fluoroscopy, where the image receptor and the image-intensifier tube are round. Additionally, the profiles can be categorized based on, for example, size, age, and gender.

Figure 8:
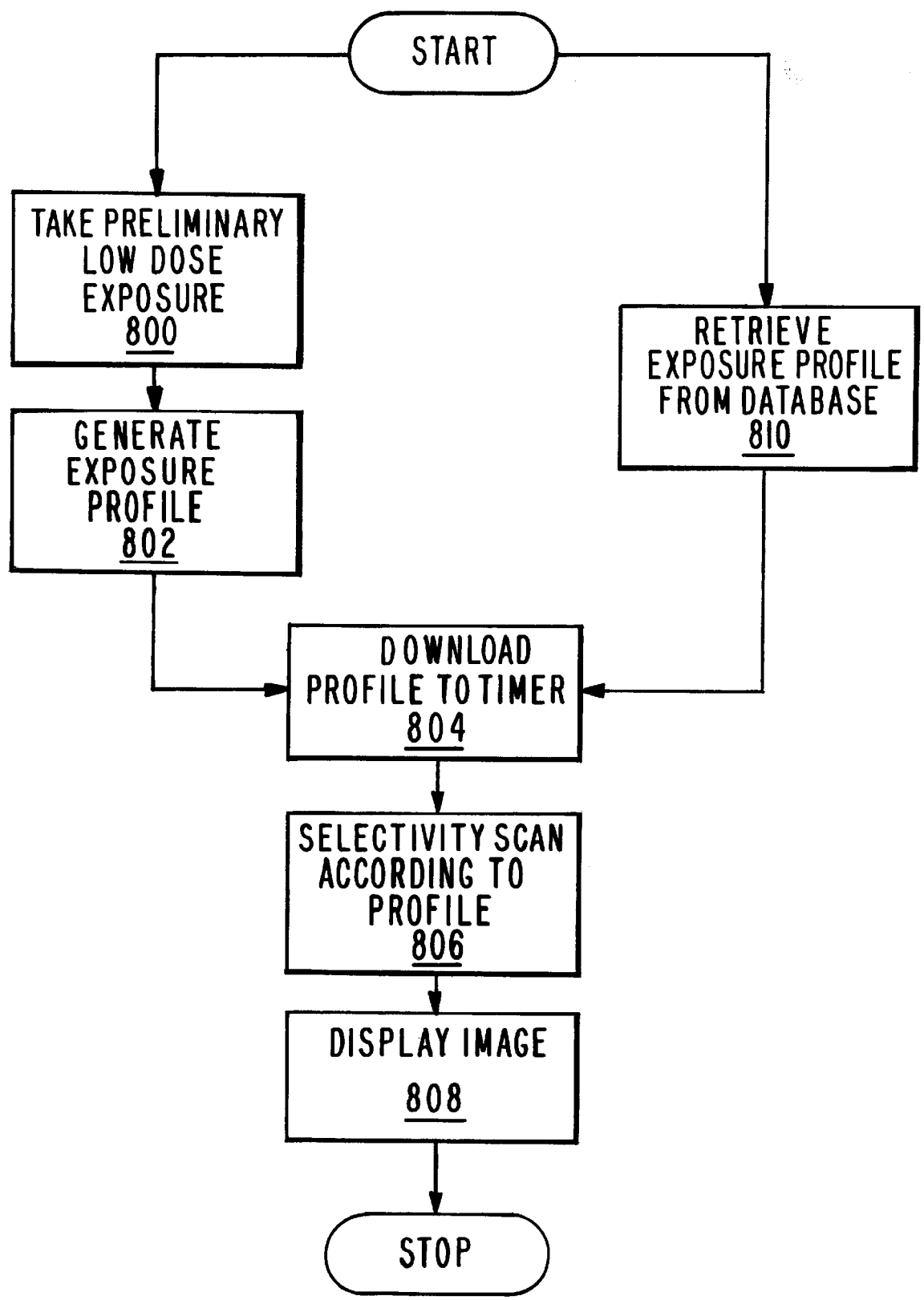
FIG. 8 is a flow diagram illustrating the use of selective scanning to generate diagnostic images having uniform optical density in accordance with the present invention.

Referring to FIG. 8, there is shown a flow diagram illustrating the generation of images having uniform optical density in accordance with the present invention. The method includes taking 800 a preliminary low dose exposure of the target anatomy to develop 802 an exposure compensation profile, as described with respect to FIGS. 6 and 7. After developing 802 an exposure compensation profile, the profile is downloaded 804 into a programmable timer for selectively scanning pixel lines in a sensor array. After downloading 804 the profile into the programmable timer, the target anatomy is exposed to x-rays and selectively scanned 806 according to the time sequences in the exposure compensation profile. The x-ray image is then captured, built into a diagnostic image, and displayed 808 to the user. Alternatively, the exposure compensation profile can be selected 810 from an existing database before being downloaded 804 into the programmable timer as shown in FIG. 8.

The above description is included to illustrate the operation of the preferred embodiments and is not meant to limit the scope of the invention. The scope of the invention is to be limited only by the following claims. From the above discussion, many variations will be apparent to one skilled in the art that would yet be encompassed by the spirit and scope of the present invention.

What is claimed is:

1. A method for compensating for x-ray exposure of a patient body part by a digital x-ray system, said digital x-ray system having a sensor array for capturing x-ray images, said method comprising the steps of:

generating exposure compensation profiles for said patient body part based on at least one physical dimension of said body part; and selectively scanning lines of pixels from said sensor array based on said exposure compensation profiles to control exposure times of said lines of pixels to said x-rays.

2. The method of claim 1, wherein said step of generating said exposure compensation profiles includes taking low dose exposures of said patient body part to determine said exposure compensation profiles.

3. The method of claim 1, wherein said step of generating said exposure compensation profiles includes using predetermined exposure compensation profiles from a database.

4. The method of claim 1, wherein said step of selectively scanning said lines of pixels includes loading an ordered sequence of exposure times into a programmable timer coupled to read out circuitry, said exposure times for controlling and sequencing said read out circuitry to selectively scan said lines of pixels while said patient body part is subjected to said x-ray exposure.

5. The method of claim 1, wherein said exposure compensation profiles are used to emulate one from the group of conventional compensating filters consisting of a "wedge" filter, a "trough" filter, a "bow-tie" filter, and a "conic" filter.

6. A digital x-ray system for compensating x-ray exposure of a patient body part, said x-ray system including a sensor unit for receiving said x-rays from an x-ray source and converting said x-rays into visible light, the sensor unit comprising:

a sensor array having a plurality of pixels for receiving said visible light;

a programmable timer coupled to said sensor array for receiving an ordered sequence of exposure times from an exposure compensation profile based on at least one physical dimension of said body part, said programmable timer for selecting said pixels in said sensor array to be scanned in accordance with said ordered sequence of exposure times; and readout circuitry coupled to said sensor array for reading out values from said selected pixels in said sensor array, said pixel values indicative of the effective light intensity on said pixels.

7. The system of claim 6, further including an analog-to-digital converter coupled to the readout circuitry for converting said pixel values into digital representations.

8. The system of claim 6, wherein said sensor unit includes a plurality of sensor arrays, and said exposure compensation profile includes exposure time sequences, each exposure time sequence corresponding to one of said plurality of said sensor arrays, each exposure time sequence including a plurality of pixel line numbers and a plurality of read out times corresponding to said pixel line numbers.

9. The system of claim 8, wherein said pixel line numbers and said read out times are generated empirically from a test series of read out sequences on a phantom image of said patient body part.

10. The system of claim 6, wherein said readout circuitry is a multiplexer.

11. Apparatus for compensating for x-ray exposure of a patient body part by a digital x-ray system, said digital x-ray system having a sensor array for capturing x-ray images, said apparatus comprising:

means for generating exposure compensation profiles for said body part based on at least one physical dimension of said body part; and means for selectively scanning lines of pixels from said sensor array based on said exposure compensation profiles to control exposure times of said lines of pixels to said x-rays.

12. The apparatus of claim 11, wherein said means for generating exposure compenstion profiles comprises means for taking load dose exposures of said patient body part.

13. The apparatus of claim 11, wherein said means for generating exposure compensation profiles comprises means for using predetermined exposure compensation profiles from a database.

14. The apparatus of claim 11, wherein said means for selectively scanning lines of pixels comprises means for loading an ordered sequence of exposure times into a programmable timer coupled to read out circuitry, said exposure times for controlling and sequencing said read out circuitry to selectively scan said lines of pixels while said patient body part is subjected to said x-ray exposure.

15. The apparatus of claim 11, further comprising means for using said exposure compensation profiles to emulate one from the group of conventional compensating filters consisting of a "wedge" filter, a "trough" filter, a "bow-tie" filter, and a "conic" filter.

* * * * *